United States Patent [19]

Weuthen

[11] Patent Number: 5,858,961
[45] Date of Patent: Jan. 12, 1999

[54] PROCESS FOR THE PRODUCTION OF LIGHT-COLORED SURFACTANTS

[75] Inventor: Manfred Weuthen, Solingen, Germany

[73] Assignee: Henkel Kommanditgesellschaft auf Aktien, Duesseldorf, Germany

[21] Appl. No.: 776,074

[22] PCT Filed: Jun. 28, 1995

[86] PCT No.: PCT/EP95/02514

§ 371 Date: Feb. 6, 1997

§ 102(e) Date: Feb. 6, 1997

[87] PCT Pub. No.: WO96/01269

PCT Pub. Date: Jan. 18, 1996

[30] Foreign Application Priority Data

Jul. 6, 1994 [DE] Germany .......................... 44 23 641.7

[51] Int. Cl.$^6$ .............................. C11D 11/00; C11D 1/14; C11D 3/22
[52] U.S. Cl. .......................... 510/535; 510/470; 510/536; 510/537; 510/495
[58] Field of Search .................................... 510/535, 536, 510/537, 470, 495

[56] References Cited

U.S. PATENT DOCUMENTS

| | | | |
|---|---|---|---|
| 4,077,911 | 3/1978 | Okumura et al. | 252/550 |
| 4,320,026 | 3/1982 | Cristobal et al. | 252/139 |
| 4,871,423 | 10/1989 | Grimsley et al. | 162/72 |
| 5,372,610 | 12/1994 | Kahle et al. | 8/111 |
| 5,374,716 | 12/1994 | Biermann et al. | 536/18.6 |
| 5,397,494 | 3/1995 | Vega et al. | 252/95 |
| 5,429,773 | 7/1995 | Sherry et al. | 252/554 |
| 5,554,742 | 9/1996 | Wolf et al. | 536/18.6 |

FOREIGN PATENT DOCUMENTS

| | | |
|---|---|---|
| 301 298 | 2/1989 | European Pat. Off. . |
| 531849 | 3/1993 | European Pat. Off. . |
| 25 24 785 | 1/1976 | Germany . |
| 41 42 592 | 6/1993 | Germany . |
| 2 274 105 | 7/1994 | United Kingdom . |
| WO 90/03977 | 4/1990 | WIPO . |
| WO 93/13112 | 7/1993 | WIPO . |
| WO 93/13113 | 7/1993 | WIPO . |
| WO 93/21196 | 10/1993 | WIPO . |
| WO 94/02494 | 2/1994 | WIPO . |
| WO 94/03423 | 2/1994 | WIPO . |

OTHER PUBLICATIONS

J. Falbe (ed.), "Surfactants in Consumer Products", Springer Verlag, Berlin, 1987, pp. 54 to 124.
J. Falbe (ed.), "Katalysatoren, Tenside und Mineralöladditive", Thieme Verlag, Stuttgart, 1978, pp. 123 to 217.
JAOCS–INFORM, vol. 67, No. 12 (Dec. 1990), pp. 1002–1007.
Fat Sci. Technol. 92, 201 (1990).
J. Am. Oil. Chem. Soc. 70, 773 (1993).

*Primary Examiner*—Mukund J. Shah
*Assistant Examiner*—Bruck Kifle
*Attorney, Agent, or Firm*—Wayne C. Jaeschke; John E. Drach; Steven J. Trzaska

[57] ABSTRACT

The invention relates to a process for the production of light-colored surfactants in which the surfactants are stabilized before bleaching by addition of antioxidants.

5 Claims, No Drawings

PROCESS FOR THE PRODUCTION OF LIGHT-COLORED SURFACTANTS

BACKGROUND OF THE INVENTION

1. Field of the invention

This invention relates to a process for the production of light-colored surfactants, in which the surfactants are stabilized before bleaching by addition of antioxidants.

2. Statement of Related Art

Most surface-active compounds of the anionic surfactant type, but also certain nonionic surfactants, such as alkyl oligoglycosides for example, are dark in color from their production, for example as a result of oxidation and condensation processes. Although this discoloration has little or no adverse effect on the performance properties of the compounds, only those compounds which have been lightened in color by subsequent bleaching are suitable for subsequent processing on aesthetic grounds. Peroxygen compounds, such as for example hydrogen peroxide, perborates or percarbonates, are normally used for this purpose, having almost completely displaced the hypochlorites often previously used.

There has been no shortage of attempts in the past further to improve the color quality of surfactants which, despite bleaching, has often been unsatisfactory. For example, it is proposed in WO 93/13113 (Henkel) to enhance the effect of the hydrogen peroxide by using various bleaching boosters, such as for example magnesium ions and the like. Although it has been found in practice that products with a distinctly improved color are obtained, their stability in storage is still far from satisfactory.

Accordingly, the problem addressed by the present invention was to remedy this deficiency by providing a process that would give products which would be light in color immediately after bleaching and which would remain stable, even after prolonged storage at —optionally —relatively high temperatures.

DESCRIPTION OF THE INVENTION

The present invention relates to a process for the production of light-colored surfactants which is characterized in that the surfactants are stabilized before bleaching by addition of antioxidants.

In one preferred embodiment, the invention relates to a process for the production of light-colored alkyl and/or alkenyl oligoglycosides by acid-catalyzed acetalization of sugars with fatty alcohols, neutralization, removal of excess fatty alcohol by distillation, forming a paste with water and alkaline bleaching, characterized in that the glycosides are stabilized before bleaching by addition of antioxidants.

In another preferred embodiment, the invention relates to a process for the production of light-colored alkyl and/or alkenylsulfates by sulfation of fatty alcohols, neutralization with aqueous bases and bleaching, characterized in that the sulfates are stabilized before bleaching by addition of antioxidants.

It has surprisingly been found that the addition of known antioxidants to water-containing surfactant pastes stabilizes the pastes during bleaching to such an extent that, on the one hand, particularly light-colored products are obtained which, on the other hand, undergo hardly any darkening in color, even after storage for several weeks at elevated temperature. The invention includes the observation that the time at which the stabilizers are added to the surfactants is critical. In particular, the addition of antioxidants after bleaching (i.e. to the retail product) is not comparable either in regard to color quality or in regard to stability in storage. The surfactants are preferably present in the form of aqueous solutions or pastes with solids contents of 5 to 50% by weight and preferably 15 to 40% by weight. Basically, however, the process according to the invention may also be applied to water-free systems.

Surfactants

The process according to the invention may be used to improve the color of anionic, nonionic, cationic and/or ampholytic or zwitterionic surfactants.

Typical examples of anionic surfactants are alkyl benzenesulfonates, alkanesulfonates, olefin sulfonates, alkylether sulfonates, glycerol ether sulfonates, α-methylester sulfonates, sulfofatty acids, alkylsulfates, fatty alcohol ether sulfates, glycerol ether sulfates, hydroxy mixed ether sulfates, monoglyceride (ether)sulfates, fatty acid amide (ether)sulfates, monoalkyl and dialkyl sulfosuccinates, monoalkyl and dialkyl sulfosuccinamates, sulfotriglycerides, amide soaps, ether carboxylic acids and salts thereof, fatty acid isethionates, fatty acid sarcosinates, fatty acid taurides, acyl lactylates, alkyl oligoglucoside sulfates and alkyl (ether)phosphates. If the anionic surfactants contain polyglycol ether chains, they may have a conventional homolog distribution, although they preferably a narrow homolog distribution.

Among the anionic surfactants to which the process according to the invention may be applied, those with a sulfate or sulfonate structure and also protein fatty acid condensates are preferred.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, alk(en)yl oligoglycosides, fatty acid N-alkyl glucamides, polyol fatty acid esters, sugar esters, sorbitan esters and polysorbates. If the nonionic surfactants contain polyglycol ether chains, they may have a conventional homolog distribution, although they preferably have a narrow homolog distribution.

Among the nonionic surfactants to which the process according to the invention may be applied, alkyl polyglucosides, methyl glucoside esters, alkyl glucoside esters, sucrose esters and oligoglycerol esters are preferred.

Typical examples of cationic surfactants are quaternary ammonium compounds and esterquats, more particularly quaternized fatty acid trialkanolamine ester salts.

Typical examples of amphoteric or zwitterionic surfactants are alkyl betaines, alkyl amido betaines, aminopropionates, aminoglycinates, imidazolinium betaines and sulfobetaines.

The surfactants mentioned are all known compounds. Information on the structure and production of these compounds can be found in relevant synoptic works, for example J. Falbe (ed.), "Surfactants in Consumer Products", Springer Verlag, Berlin, 1987, pages 54 to 124 or J. Falbe (ed.), "Katalysatoren, Tenside und Mineralöl-additive", Thieme Verlag, Stuttgart, 1978, pages 123 to 217.

Alkyl and/or alkenyl oligoglycosides

Alkyl and alkenyl oligoglycosides are known substances which correspond to formula (I):

in which $R^1$ is an alkyl and/or alkenyl radical containing 4 to 22 carbon atoms, G is a sugar unit containing 5 or 6 carbon atoms and p is a number of 1 to 10. The glycosides may be obtained by the relevant methods of preparative organic chemistry. EP-A1- 0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the 20 degree of oligomerization (DP degree), i.e. the distribution of mono- and oligoglycosides, and is a number of 1 to 10. Whereas p in a given compound must always be an integer and, above all, may assume a value p of 1 to 6, the value p for a certain alkyl oligoglucoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and technical mixtures thereof such as are obtained, for example, in the hydrogenation of technical fatty acid methyl esters or in the hydrogenation of aldehydes from Roelen's oxo synthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, and technical mixtures thereof which may be obtained as described above. Alkyl oligoglucosides based on hydrogenated $C_{12/14}$ coconut oil fatty alcohol having a DP of 1 to 3 are preferred.

Alkyl and/or alkenylsulfates

Alkyl and/or alkenylsulfates in the context of the invention are the sulfation products of primary alcohols which correspond to formula (II):

$$R^2O—SO_3X \quad (II)$$

in which $R^2$ is a linear or branched aliphatic alkyl and/or alkenyl radical containing 6 to 22 and preferably 12 to 18 carbon atoms and X is an alkali metal and/or alkaline earth metal, ammonium, alkylammonium, alkanolammonium or glucammonium.

Typical examples of alkylsulfates which may be used in accordance with the invention are the sulfation products of caproic alcohol, caprylic alcohol, capric alcohol, 2-ethylhexyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol and erucyl alcohol and the technical mixtures thereof obtained by high-pressure hydrogenation of technical methyl ester fractions or aldehydes from Roelen's oxo synthesis. The sulfation products may advantageously be used in the form of their alkali metal salts, more particularly their sodium salts. Alkylsulfates based on $C_{16/18}$ tallow fatty alcohols or vegetable fatty alcohols with a comparable C chain distribution in the form of their sodium salts are particularly preferred.

Antioxidants

Antioxidants or (aut)oxidation inhibitors are generally understood to be substances which prevent or at least inhibit unwanted changes in the materials to be stabilized caused by the effect of oxygen and by other oxidative processes. The effect of antioxidants is generally based on the fact that they act as radical scavengers for the free radicals occurring during the autoxidation process [cf. INFORM, 1, 1002 (1990) ]. Typical examples of antioxidants are:

Phenols and phenol derivatives such as, for example, tert.butyl hydroxytoluene (BHT), ditert.butyl hydroxytoluene (DBHT), ditert.butyl hydroxyanisole (BHA), hydroquinone, ethoxyquin, tert.butyl hydroxy-quinone, ditert.butyl hydroxyquinone, anoxomer, gallic acid, gallic acid ester, rosemary diphenol, boldine and α-, β- and γ-tocopherol and acetates thereof [cf. Fat Sci. Technol. 92, 201 (1990)].

Hydroxycarboxylic acids, salts and alkylesters thereof, such as for example lactic acid, malic acid, citric acid, tartaric acid, ascorbic acid and ascorbyl palmitate;

Flavenoids such as, for example, catechol, hespiritin, morin, naringin, quercitin and rutin [cf. J. Am. Oil. Chem. Soc. 70, 773 (1993)];

Fatty acid amides, pyridine compounds and alkali metal nitrites.

Antioxidants selected from the group consisting of tocopherol, BHT, BHA, ascorbic acid, ascorbyl palmitate, citric acid and/or alkali metal nitrites are preferably used. Of these antioxidants, tocopherols are particularly preferred. The antioxidants may normally be used in concentrations of 5 to 2,000 ppm, preferably in concentration of 25 to 1,000 ppm and more preferably in concentrations of 50 to 200 ppm, based on the sum of the starting materials. In one preferred embodiment of the invention, the antioxidants may be combined with known bleaching boosters, such as for example magnesium salts, zeolites, hydrotalcite, alkali metal silicates and the like.

If alkyl glucoside pastes are stabilized, the stabilizers may be added to the pastes before or after distillation of the excess fatty alcohol. In the case of anionic surfactants with a sulfate and/or sulfonate structure, the stabilizers may be added before or after the neutralization step. In both cases, however, the stabilizers must be added before bleaching.

Industrial Applications

The surfactants obtainable by the process according to the invention are distinguished by a particularly advantageous color quality and remain stable, even after storage for several weeks at elevated temperature. They are suitable for the production of surface-active preparations such as, for example, laundry detergents, dish-washing detergents and cleaning products in which they may be present in quantities of 1 to 50% by weight and preferably 5 to 25% by weight, based on the particular preparation.

EXAMPLES

I. Production of an alkyl polyglucoside paste 900 g (5 moles) of anhydrous glucose were introduced into a 5 liter distillation assembly and mixed with 1,820 g (12.5 moles) of a technical 1:1 mixture of octanol and decanol (LOROL® 810, a product of Henkel KGaA, Düsseldorf, FRG). 10.4 g (0.004 mole) of p-toluene sulfonic acid in the form of a 65% by weight aqueous solution were added dropwise at a temperature of 100° C. under a reduced pressure of 45 mbar and the water released during the acetalization was continuously removed from the reaction mixture. After 8 h, the mixture was cooled to 80° C. and purged with nitrogen. It was then neutralized with 1.5 ml (0.03 mole) of 50% by weight sodium hydroxide solution and 2 g (0.05 mole) of magnesium oxide.

After 120 minutes, the antioxidant was added to the mixture (variant 1) and the excess fatty alcohol was distilled off at a temperature of 160° C. and under a reduced pressure of 0.1 mbar.

140 g of the solid reaction product were then dissolved in 75 g of water at 80° C. The antioxidant and 4 ml of a 50% by weight sodium hydroxide solution were added to the dark-colored paste (variant 2). Finally, 5.5 ml of hydrogen peroxide in the form of a 35% by weight solution were added at a temperature of 90° C., followed by stirring for 4 h. The pH value was adjusted to 11.5 by addition of sodium hydroxide solution.

Table 1 below shows the color values; after storage for 24 h, 2 weeks and 4 weeks at 70° C. in dependence upon the antioxidants used. For Comparison Example C2, Example 1 was repeated except that the tocopherol was added to the retail product after alkaline bleaching.

TABLE 1

Color values of alkyl polyglucoside pastes*

| Ex. | Antioxidant | c(An) ppm | V | Color value [Gardner] 24 h | 2 w | 4 w |
|---|---|---|---|---|---|---|
| 1 | Tocopherol | 1000 | 1 | 2 | 2 | 3 |
| 2 | Tocopherol | 500 | 2 | 2 | 2 | 2 |
| 3 | BHT | 500 | 1 | 2 | 2 | 2 |
| 4 | BHA | 500 | 1 | 2 | 2 | 2 |
| 5 | Ascorbyl palmitate | 500 | 1 | 3 | 3 | 4 |
| 6 | Ascorbic acid | 500 | 1 | 3 | 3 | 4 |
| 7 | Citric acid | 500 | 1 | 3 | 3 | 5 |
| 8 | Ascorbic acid + Citric acid | 400 100 | 1 | 2 | 2 | 3 |
| 9 | Sodium nitrite | 50 | 1 | 3 | 3 | |
| C1 | None | — | — | 15 | 20 | 20 |
| C2 | Tocopherol | 1000 | — | 8 | 12 | 15 |

*2 cm cuvette

II. Production of an alkylsulfate paste 5.0 Moles of a fatty alcohol mixture corresponding to product A with a melting point of 43° C. were reacted at 55° C. with 5.35 moles of gaseous sulfur trioxide (alcohol:$SO_3$=1:1.07) in a continuous falling-film reactor (length 120 cm, cross-section 1 cm, educt throughput 600 g/h) equipped with a jacket cooling system and a lateral inlet for $SO_3$ gas. The acidic reaction mixture was continuously introduced into 25% by weight aqueous sodium hydroxide solution and thus neutralized, after which the antioxidant was added, the reaction mixture was subsequently bleached with 2% by weight of hydrogen peroxide in the form of a 35% by weight aqueous solution and, finally, was adjusted to a pH value of 10.9.

Table 2 below shows the color values after storage for 24 h, 2 weeks and 4 weeks at 70° C. in dependence upon the antioxidants used.

TABLE 2

Color values of alkylsulfate pastes*

| Ex. | Antioxidant | c(An) ppm | Color value [Klett] 24 h | 2 w | 4 w |
|---|---|---|---|---|---|
| 10 | Tocopherol | 500 | 11 | 15 | 21 |
| 11 | BHT | 500 | 14 | 15 | 22 |
| 12 | BHA | 500 | 12 | 15 | 22 |
| 13 | Ascorbyl palmitate | 500 | 14 | 15 | 23 |
| 14 | Ascorbic acid | 500 | 14 | 15 | 24 |
| 15 | Citric acid | 500 | 14 | 16 | 25 |
| 16 | Ascorbic acid + Citric acid | 400 100 | 12 | 15 | 23 |
| C2 | None | — | 42 | 57 | 78 |

Legend:
c(An) = concentration of antioxidant
*4 cm cuvette

I claim:

1. An improved process for the production of light-colored surfactants which comprises contacting a surfactant with a bleaching agent wherein the improvement comprises contacting said surfactant with an effective amount of an antioxidant selected from the group consisting of BHT, BHA, ascorbic acid ascorbyl palimate, an alkali metal nitrite, and mixtures thereof, prior to bleaching.

2. The process of claim 1 wherein said surfactant is in the form of an aqueous paste.

3. The process of claim 1 wherein the amount of said antioxidant is from about 5 to about 2,000 ppm.

4. The process of claim 1 wherein the surfactant is an alkyl and/or alkenyl oligoglycoside.

5. The process of claim 1 wherein the surfactant is an alkyl and/or alkenylsulfate.

* * * * *